(12) United States Patent
Marsh et al.

(10) Patent No.: US 7,645,264 B2
(45) Date of Patent: Jan. 12, 2010

(54) INJECTION DEVICE WITH SECONDARY RESERVOIR

(75) Inventors: Ronald W. Marsh, Hackettstown, NJ (US); Mark Follman, Glen Rock, NJ (US); Edward P. Browka, Chapel Hill, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 670 days.

(21) Appl. No.: 11/102,874

(22) Filed: Apr. 11, 2005

(65) Prior Publication Data

US 2006/0229562 A1 Oct. 12, 2006

(51) Int. Cl.
*A61M 5/00* (2006.01)
*A61M 5/32* (2006.01)
*A61M 15/00* (2006.01)

(52) U.S. Cl. ............... 604/117; 604/411; 604/192; 128/200.24

(58) Field of Classification Search ............ 435/69.1, 435/69.3, 190, 193, 196, 220; 604/506, 175, 604/28, 46, 502, 192, 239, 68, 70, 131, 288.02; 536/23.5, 23.4; 424/193.1

See application file for complete search history.

(56) References Cited

U.S. PATENT DOCUMENTS

| | | | |
|---|---|---|---|
| 4,583,978 A | 4/1986 | Porat et al. | |
| RE32,974 E | 7/1989 | Porat et al. | |
| 5,078,691 A | 1/1992 | Hamacher | |
| 5,281,198 A * | 1/1994 | Haber et al. | 604/86 |
| 5,378,233 A | 1/1995 | Haber et al. | |
| 5,505,694 A | 4/1996 | Hubbard et al. | |
| 5,514,097 A * | 5/1996 | Knauer | 604/136 |
| 5,984,906 A * | 11/1999 | Bonnichsen et al. | 604/272 |
| 6,203,529 B1 * | 3/2001 | Gabriel et al. | 604/192 |
| 6,364,865 B1 * | 4/2002 | Lavi et al. | 604/411 |
| 6,494,865 B1 | 12/2002 | Alchas | |
| 6,558,402 B1 | 5/2003 | Chelak et al. | |
| 6,569,143 B2 | 5/2003 | Alchas et al. | |
| 6,589,209 B1 | 7/2003 | Dysarz | |
| 6,942,645 B2 * | 9/2005 | Alexandre et al. | 604/68 |
| 7,077,827 B2 * | 7/2006 | Greenfield | 604/191 |
| 2003/0050602 A1 * | 3/2003 | Pettis et al. | 604/117 |
| 2005/0000514 A1 * | 1/2005 | Sullivan et al. | 128/200.24 |

FOREIGN PATENT DOCUMENTS

| | | |
|---|---|---|
| WO | WO 02-02179 A1 | 1/2002 |
| WO | WO 2004-108193 A1 | 12/2004 |
| WO | WO 2005-025641 A2 | 3/2005 |

\* cited by examiner

*Primary Examiner*—Nicholas D Lucchesi
*Assistant Examiner*—Ian K Holloway
(74) *Attorney, Agent, or Firm*—David M. Fortunato; Roylance, Abrams, Berdo & Goodman LLP

(57) ABSTRACT

A method and apparatus for injecting fluid into areas having high density tissue that creates a high backpressure resistance on the injection device is disclosed. The high backpressure resistance is overcome through a mechanical advantage achieved by using a secondary reservoir having a cross-sectional area smaller than the cross-sectional area of a primary reservoir. Exemplary injection device reservoir housings may comprise a primary reservoir, a secondary reservoir, a check valve, a septum penetrating cannula, travel limits, a pen needle connecting portion, sliding seal guide ribs, a sliding seal, a pen needle assembly, a needle stop, and a patient needle.

23 Claims, 13 Drawing Sheets

INJECTION DEVICE WITH SECONDARY RESERVOIR

CROSS-REFERENCE TO RELATED APPLICATION

The subject matter of this application is related to that of U.S. Patent Publication No. 2005/0050602 of Pettis et al., filed Sep. 11, 2002, the entire disclosure of which is hereby incorporated by reference. The subject matter of this application is also related to that of U.S. Patent Publication No. 2006/0229570 of Lovell et al., filed Apr. 11, 2005, the entire disclosure of which is incorporated herein by reference.

FIELD OF THE INVENTION

The present invention relates generally to the delivery of medication using injection devices. Specifically, one implementation of the invention relates to injection devices and methods that incorporate a secondary pre-delivery reservoir in a microneedle medication delivery device to provide a mechanical advantage.

BACKGROUND OF THE INVENTION

In certain circumstances, it is desirable to inject medication directly into human tissue. Typically, syringes are used to inject medicaments into tissue areas, such as the intramuscular tissue layer, the subcutaneous tissue layer, and the intradermal tissue layer. Each of these tissue layers has specific characteristics that affect the amount of fluid pressure needed to inject a fluid into the targeted tissue layer. When injecting fluids into each of these tissue layers, the user must exert enough force on the injection device to overcome different amounts of backpressure associated with the particular tissue layer. In general, practitioners and self-injectors, such as diabetics, are familiar with the force necessary to inject fluids into the subcutaneous layer. Injections into the subcutaneous and intramuscular tissue layers can cause discomfort to the patient or self-injector because of the characteristics of the tissue, needle length and needle diameter or gauge. It is desirable to employ shorter, smaller gauge needles to achieve delivery into the intradermal tissue layer.

It is noted that when the needle lengths are shortened and needle diameters are made smaller, the fluid dynamics of the injection device changes. Additionally, the fluid dynamics between the injection device and the targeted tissue layer also change because the shorter needle length injects the fluid into a different tissue layer, such as the intradermal layer. Since the tissue density between the intramuscular, subcutaneous, and intradermal tissue layers varies, the ease with which fluid may be injected into each type of tissue layer varies. The variation in tissue density causes changes in the backpressure exerted by the tissue against the fluid when it is injected. For instance, the backpressure associated with the intradermal tissue layer is greater than the backpressure associated with the subcutaneous tissue layer.

Currently, several pen injection systems are commercially available for subcutaneous substance delivery of medication. These pen injection systems typically use 29 to 31 gauge needles having lengths of between 5 mm and 12.7 mm, and are used to deliver the contents of a medicament cartridge, such as insulin, to the subcutaneous tissue layers of a patient rapidly and conveniently. The medicament cartridges are generally of a standard volume and size (including a fixed cross sectional area). The pressure of delivery is the quotient of the actuation force exerted by a user and the cross sectional area of the cartridge. Since the cross-sectional area of the cartridge is fixed, higher delivery pressures require higher actuation forces by the user.

A "microneedle" pen system has been developed that reduces the pain and sensation to the user normally experienced with subcutaneous substance delivery. Such "microneedle" drug delivery systems may include shorter needles, typically less than or equal to 3 mm, with smaller diameters, in the range of 30 to 34 gauge or thinner. Such needle length and gauge size combinations are desirable to provide for sharp, yet short, point geometries that can more accurately target substance delivery to only certain selected tissue, such as the deep intradermal or shallow subcutaneous tissue layers, thereby permitting controlled fluid delivery. Current typical pen injection systems used for subcutaneous delivery are not believed optimal for use by the general population of self-injectors for delivery into the intradermal layer because of, inter alia, the high backpressures associated with injecting fluid into the intradermal layers of the skin using microneedles.

To achieve effective medication delivery to the targeted tissue layer in light of higher backpressures, it is desirable to control two factors: the depth accuracy of the injection and the rate of the injection. This is of particular interest in connection with intradermal injections because the backpressures are relatively high, but similar analysis can be applied when injecting into the intramuscular or the subcutaneous tissue layers. The delivery of medicament within the narrow depth range of the intradermal tissue layer should first be assured, and maintained during injection. Once the depth accuracy is obtained, the rate of injection should be controlled to minimize or eliminate leakage of the medicament into other tissue layers or back out through the skin. Additional details of intradermal drug delivery and microneedles are described in U.S. Pat. No. 6,494,865, issued on Dec. 17, 2002, U.S. Pat. No. 6,569,143, issued on May 27, 2003, U.S. Pat. No. 7,186,222, issued on Mar. 6, 2007, PCT Application No. 2004/02783, filed Jan. 30, 2004, and U.S. Patent Publication No. 2005/0065472, published Mar. 24, 2005, all of which are assigned to Becton, Dickinson and Company, and the entire content of each such patent and published patent application being incorporated herein by reference.

The intradermal tissue layer of the skin is considerably denser than the subcutaneous tissue region. The density of the intradermal tissue layer on a particular patient is, in part, a function of their collagen make-up, which is affected by the patient's age, and the location of the injection site on the patient's body. This increased density of the intradermal tissue layer can create a greater backpressure resistance on the injection device than the resistance created when injecting into the subcutaneous tissue region. To overcome the increased backpressure resistance when injecting into the intradermal tissue layer with a conventional pen system, the user or patient would need to exert greater actuation force (which could be substantial) on the injector device actuator or employ some sort of powered injector device. In these applications, the injector device must be designed to withstand the greater backpressure from the intradermal injection site as well as the additional force exerted by the user or patient. Further, the increased actuation force required to actuate the injector device may result in the fluid "jetting" past the desired tissue depth due to the increased fluid pressure.

Conventional pen-type injection systems may require that the user keep the needle seated in the skin for a period of up to about 10 seconds, after the injection has been completed, to allow for the "axial compliance" of the pen mechanism (or lead screw) and the cartridge back-end stopper to equilibrate to minimize "drool" from the needle tip upon withdrawal. Such time periods may need to be increased to accommodate any additional axial compliance resulting from higher backpressures.

Therefore, a need exists to provide a system and method for enabling users or patients to inject compounds, such as therapeutic drugs, vaccines, and diagnostic materials, at a controlled rate into the intradermal tissue layer while still exerting forces similar to that required for injecting medication into the subcutaneous tissue region.

SUMMARY OF THE INVENTION

An object of one aspect of the present invention is to provide an injection device that can inject medication into the intradermal tissue layer with a comparable amount of force as that required to inject medication into the subcutaneous tissue region.

An object of another aspect of the present invention is to provide an injection device, which has a secondary reservoir that creates a mechanical advantage for injecting medication into the intradermal space.

A further objective of an aspect of the present invention is to provide for insuring the proper dosage of the medicament is delivered into the dense layer of the intradermal tissue by reducing or eliminating leakage back out through the skin surface.

Another object of yet another aspect of the present invention is to provide an injection device which has a fluid delivery mechanism that can provide the high pressures necessary to overcome the backpressure resistance encountered with fluid delivery to the intradermal or near dermal tissue layers, that can withstand the pressurization inherent in fluid delivery to the targeted tissue layer, and can be easily actuated by the user to deliver the fluid.

Another objective of other aspects of the present invention is to provide acceptable injection fluid pressures into the intradermal layer to allow for the delivery of medication at a more controlled rate of injection by allowing the user to actuate the device with an amount of force similar to injecting into other tissue regions.

In accordance with one implementation of the invention, an injection mechanism and method are provided for injecting medication into the intradermal layers of the skin using a device with a mechanical advantage derived from a secondary reservoir with a cross-sectional area that is reduced with respect to the primary reservoir.

The secondary reservoir used in an embodiment of the present invention provides a means to augment and improve upon the performance of the standard pen, syringe injector devices, or any devices with a primary reservoir or cartridge by providing a mechanical advantage desirable to reduce the actuation force required of the user. Such benefits are particularly desirable when injecting into denser tissue layers, but can be useful when injecting into other tissue spaces or other body masses, as well. The higher injection pressures achieved by the embodiments of the instant invention permit users or patients to perform injections into dense tissue layers while applying forces that are typically encountered with injections into less dense tissue layers. In addition, the higher injection forces generated through the secondary reservoir can act to counter the higher backpressures created by the denser tissue layers. These improvements allow users and patients to effect consistent and convenient delivery to the targeted tissue layer.

Another attribute of a device comprising a secondary reservoir as described herein is the reduction in compliance of the delivery system normally experienced with pen-type injector devices. As described more fully below, medicament flows from a medicament cartridge to the secondary reservoir under no backpressure, which reduces the internal forces that can cause compliance within the delivery system.

Further, the volume of the secondary reservoir may be designed to be smaller than the primary reservoir or medicament cartridge. Such a design would limit the maximum dose that may be given with a single injector stroke. Therefore, it provides an additional safeguard to help prevent overdosing of medicaments.

Further objectives and advantages, as well as the structure and function of preferred embodiments, will become apparent from consideration of the following description, drawings and examples.

BRIEF DESCRIPTION OF THE DRAWINGS

These and other objects, advantages and novel features of the invention will be more readily appreciated from the following detailed description when read in conjunction with the accompanying drawings, in which.

Throughout the drawings, it should be understood that like reference characters are used to refer to like features, elements and structures.

DETAILED DESCRIPTION OF EXEMPLARY EMBODIMENTS

Figure 1:
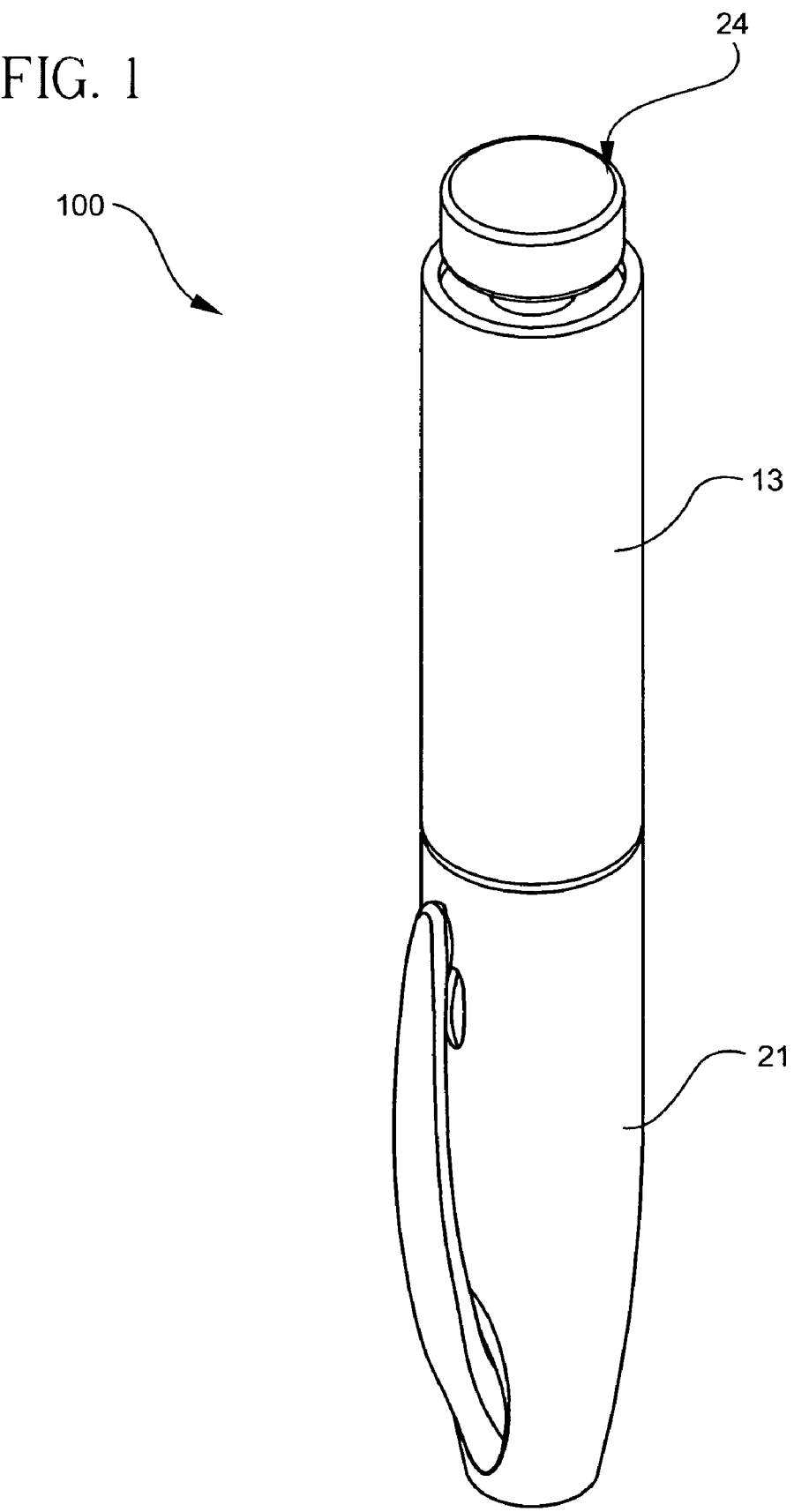
FIG. 1 is a perspective view of a pen injection device according to an embodiment of the present invention.

Pen injector devices, such as the exemplary pen injector 100, as shown in FIG. 1, typically comprise a dose knob/ button 24, an outer sleeve 13, and a cap 21. The dose knob/ button 24 allows a user to set the dosage of medication to be injected. The outer sleeve 13 is gripped by the user when injecting medication. The cap 21 is used by the user to securely hold the pen injector device 100 in a shirt pocket, purse or other suitable location.

Figure 2:
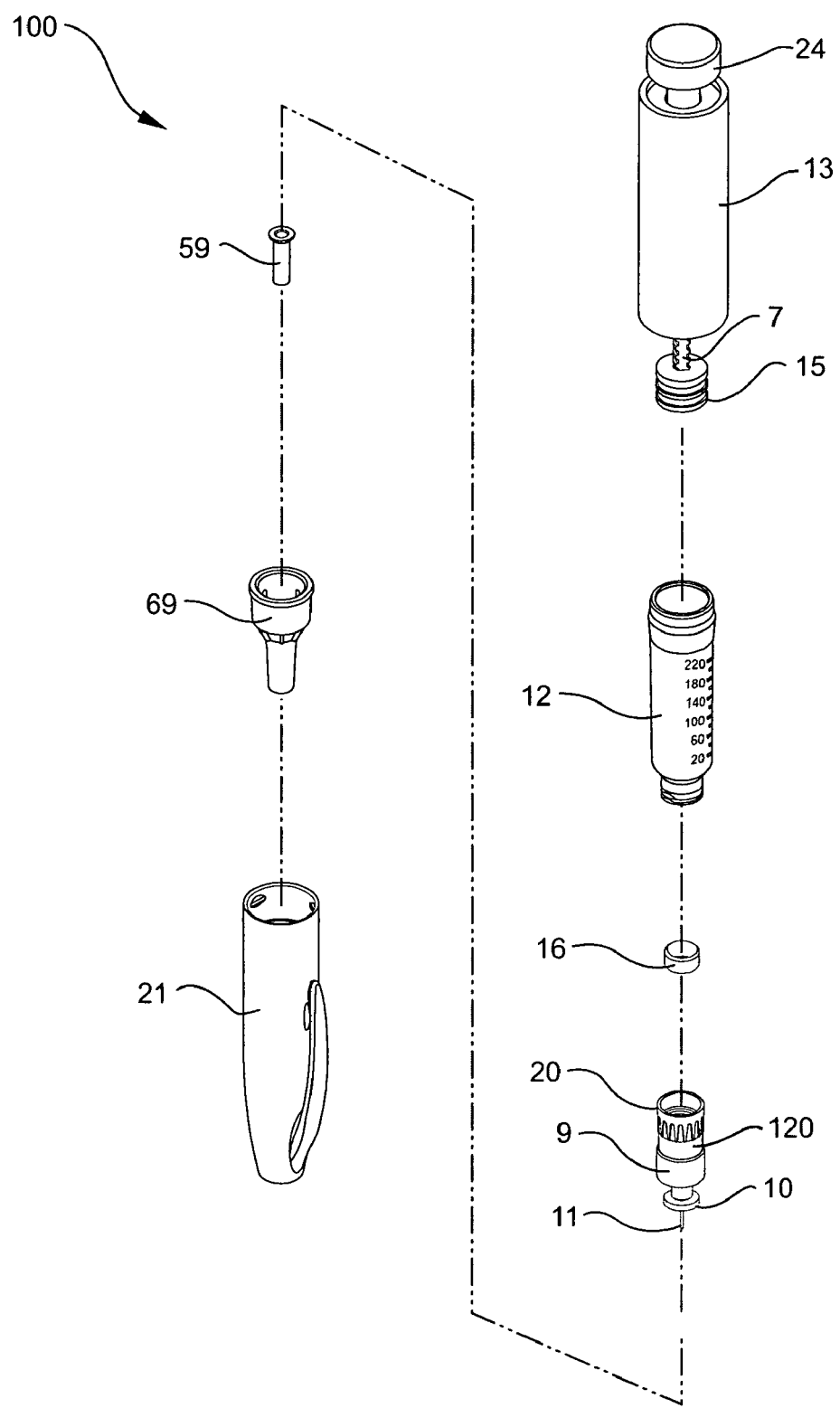
FIG. 2 is an exploded view of the components of a pen injection device according to an embodiment of the present invention.

FIG. 2 is an exploded view of an exemplary pen injector device shown in FIG. 1. The dose knob/button 24 has a dual purpose and is used to both set the dosage of the medication to be injected and used to inject the dosed medication via the lead screw 7 and stopper 15 through the medicament cartridge 12 attached to the invention through the reservoir housing 20. In standard pen injector devices the dosing and delivery mechanisms are all found within the outer sleeve 13 and are not described in greater detail here as they are understood by those knowledgeable of the prior art. The medicament cartridge 12 is typically attached to a standard pen injector housing via known attachment means such as ¼ turn fastening features. The distal movement of the plunger or stopper 15 within the medicament cartridge 12 causes medication to be forced into the reservoir housing 20. The medicament cartridge 12 is sealed by septum 16, which is punctured by a septum penetrating needle cannula 4 (shown in FIG. 4) located within reservoir housing 20. Reservoir housing 20 is preferably screwed onto the medicament cartridge 12, although other attachment means can be used. A patient needle 11 is partially covered by needle stop 10, which preferably snap-fits to a pen needle assembly 9. A front sleeve 120 is located above the pen needle assembly 9. To protect a user, or anyone who handles the pen injection device 100, an outer shield 69, which attaches to the pen needle assembly 9, covers the needle stop 10. An inner shield 59 covers the patient needle 11 within the outer shield 69. The inner shield 59 can be secured to needle stop 10, covering patient needle 11 by any suitable means, such as an interference fit or a snap-fit. The outer shield 69 and inner shield 59 are removed prior to use. The cap 21 fits snuggly against outer sleeve 13 to allow a user to securely carry the pen injection device 100.

Figure 3:
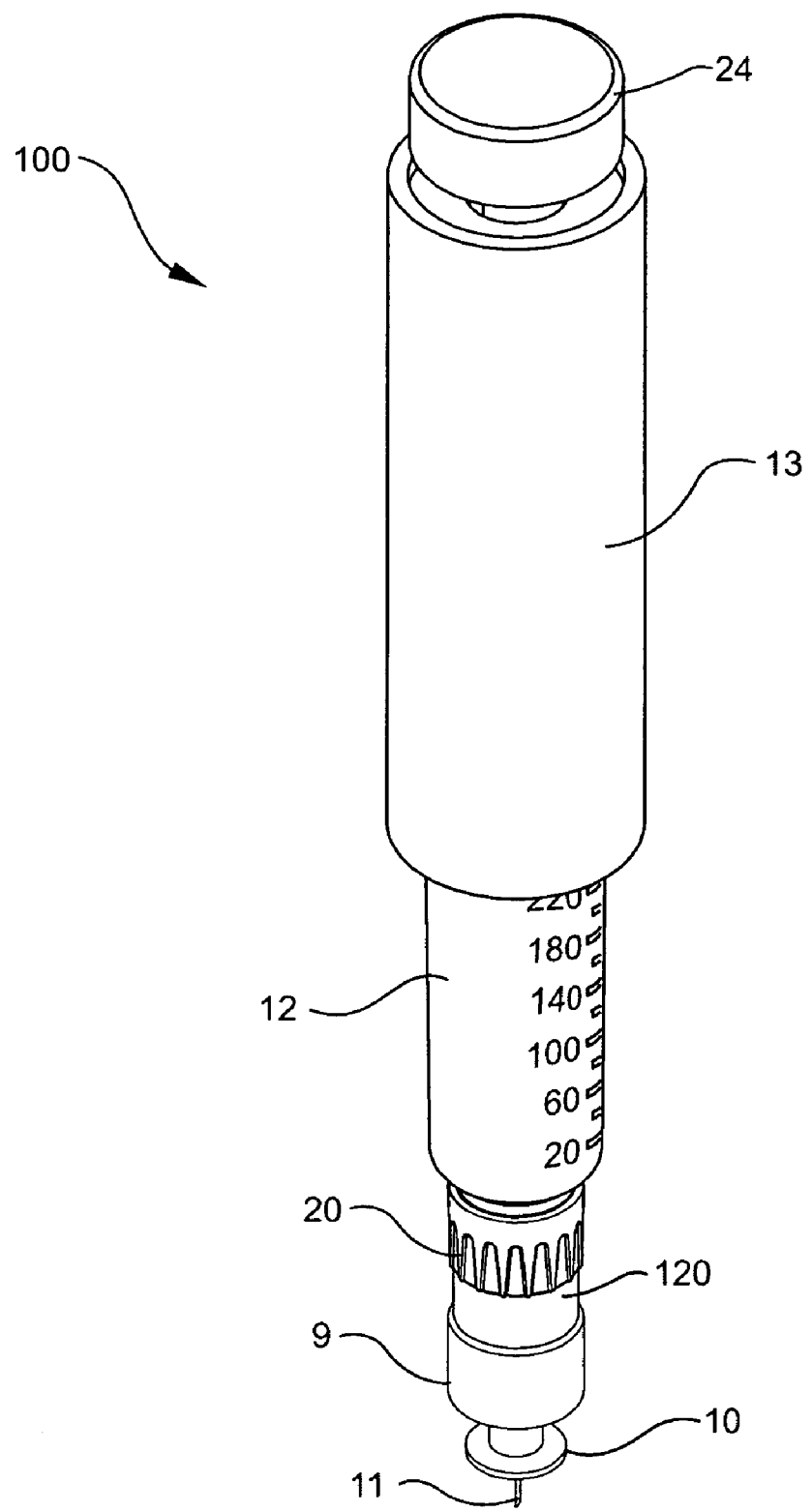
FIG. 3 is a perspective view of the pen injection device of FIG. 1 with the cap removed according to an embodiment of the present invention.

FIG. 3 is a perspective view of the pen injection device 100 with the cap 21, outer shield 69 and inner shield 59 removed. FIG. 3 demonstrates the alignment of the patient needle 11, needle stop 10, pen needle assembly 9, front sleeve 120, reservoir housing 20, medicament cartridge 12, outer sleeve 13 and dose knob/button 24 with the secondary reservoir 2 (shown in FIG. 4) in a fully collapsed, pre-dosed state.

Figure 4:
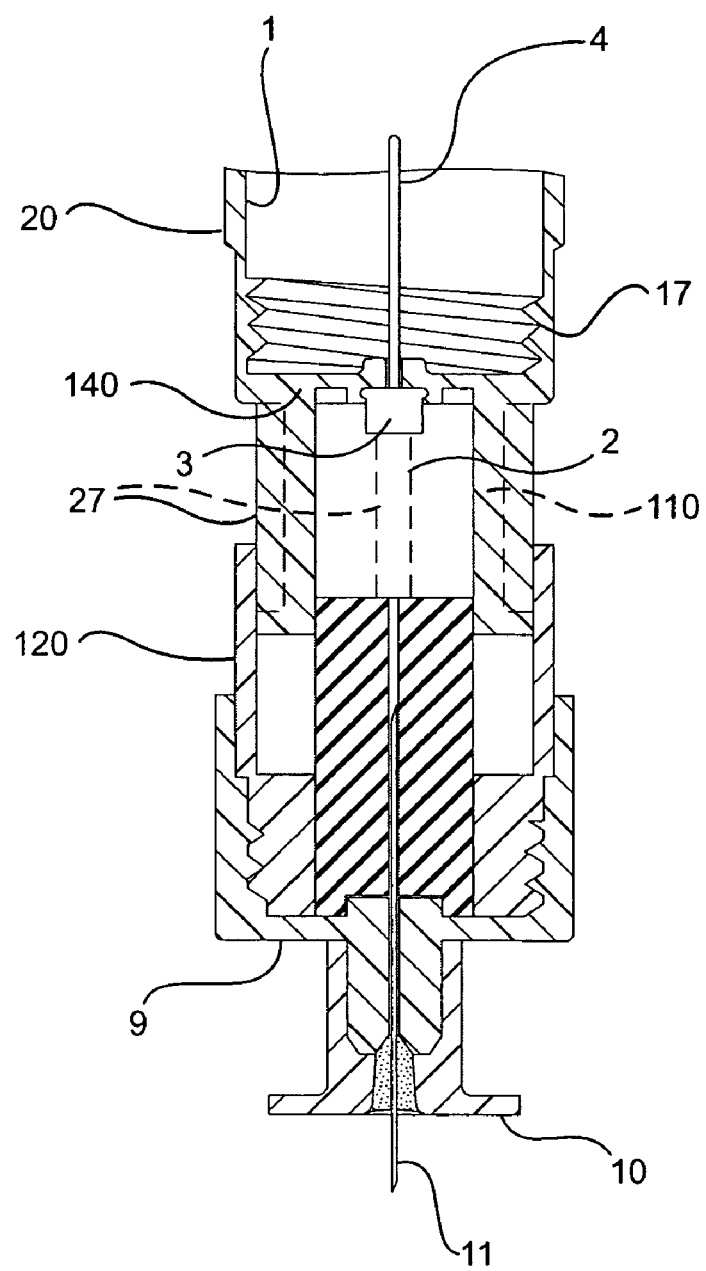
FIG. 4 is a cross-sectional view of the injection mechanism reservoir housing according to an embodiment of the present invention.

FIG. 4 is a cross-sectional view of the distal end of the pen injection device 100 according to an embodiment of the present invention. The distal end of the pen injection device 100 comprises the reservoir housing 20, the pen needle assembly 9, patient needle 11, and needle stop 10. The reservoir housing 20 comprises a primary reservoir 1 and the secondary reservoir 2. A medial wall 140 is disposed between the primary reservoir 1 and the secondary reservoir 2. As discussed more fully below, the primary reservoir 1 is adapted to receive a medicament cartridge (shown in FIG. 6) or other medication providing receptacle. Throughout the application, the medication providing receptacle, whether it be a medicament cartridge or other containment means, will be referred to as the primary reservoir 1 unless otherwise noted. It will be appreciated that, in certain applications, it will be desirable to maintain the medicament within the primary reservoir 1 without the use of a separate medicament cartridge. The primary reservoir 1 (whether formed by the medicament cartridge or the housing alone) preferably holds several doses of the medication to be administered over the course of a specified time period, such as one day or one week. As depicted, internal integral threads 17 are provided within the primary reservoir 1 to engage the medicament cartridge (shown in FIG. 6).

Figure 5:
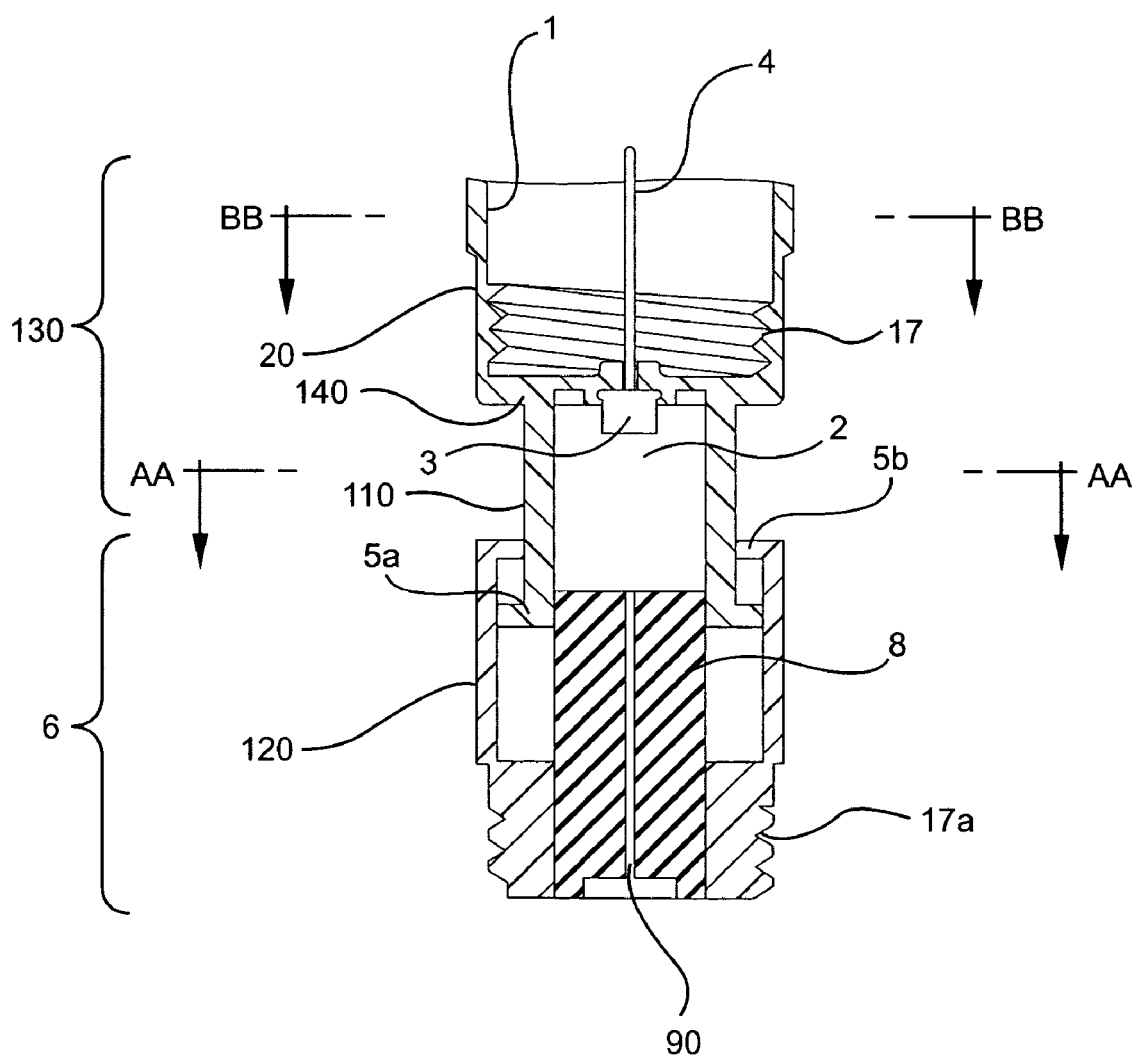
FIG. 5 is a detailed cross-sectional view of the primary and secondary reservoir of the injection mechanism reservoir housing shown in FIG. 4.
Figure 6:
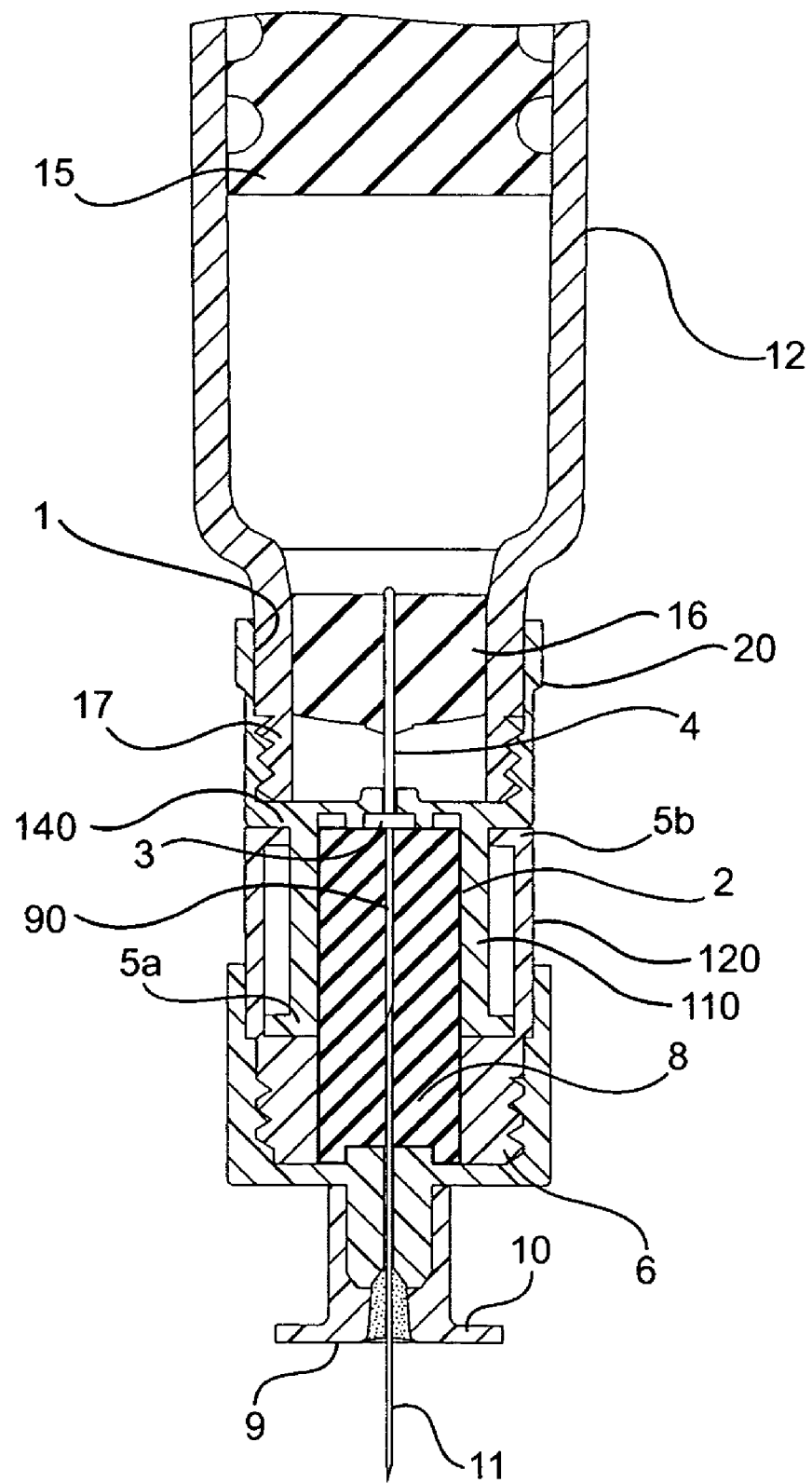
FIG. 6 is a view of the injector device in the initial pre-dosed and pre-loaded state according to an embodiment of the present invention.

As shown in FIG. 4 through FIG. 6, the secondary reservoir 2 is directly connected to the primary reservoir 1. It will be appreciated that the primary 1 and secondary 2 reservoirs may be fluidly connected by other means, such as tubing, channels or the like. The septum penetrating cannula 4 is provided to puncture a medicament cartridge septum 16 and check valve 3 prevents fluid from entering back into the medicament cartridge 12 from the secondary reservoir 2. The pen needle assembly 9 is preferably screwed on to the threads on the reservoir housing 20, which match the threads of the pen needle assembly 9. The pen needle assembly 9 can connect to the reservoir housing 20 by other suitable attachment means, such as a snap-fit. The pen needle assembly 9 preferably further comprises patient needle 11. The patient needle 11 is preferably affixed to the pen needle assembly 9 by an adhesive, epoxy or other suitable means. Needle stop 10 preferably has an area through which patient needle 11 passes as the needle stop 10 is attached to pen needle assembly 9. The needle stop 10 can be attached to pen needle assembly 9 by snap-fit, screw threads, or other suitable means. Alternatively, the needle stop 10 can be integrally formed with pen needle assembly 9. An embodiment of the invention is shown in FIG. 4, in which the reservoir housing 20, the front sleeve 120, the pen needle assembly 9, the needle stop 10 and the patient needle 11 are depicted through guide ribs 27, described in greater detail below, with the secondary reservoir 2, which is in a dosed state, and a substantially open check valve 3.

Another feature of the reservoir housing 20, shown in FIG. 5, is that the cross-sectional area of section BB of the primary reservoir 1 is larger than the cross-sectional area of section AA of the secondary reservoir 2. The advantages of the different cross-sectional areas between the primary and secondary reservoirs will be explained in greater detail below.

Figure 10:
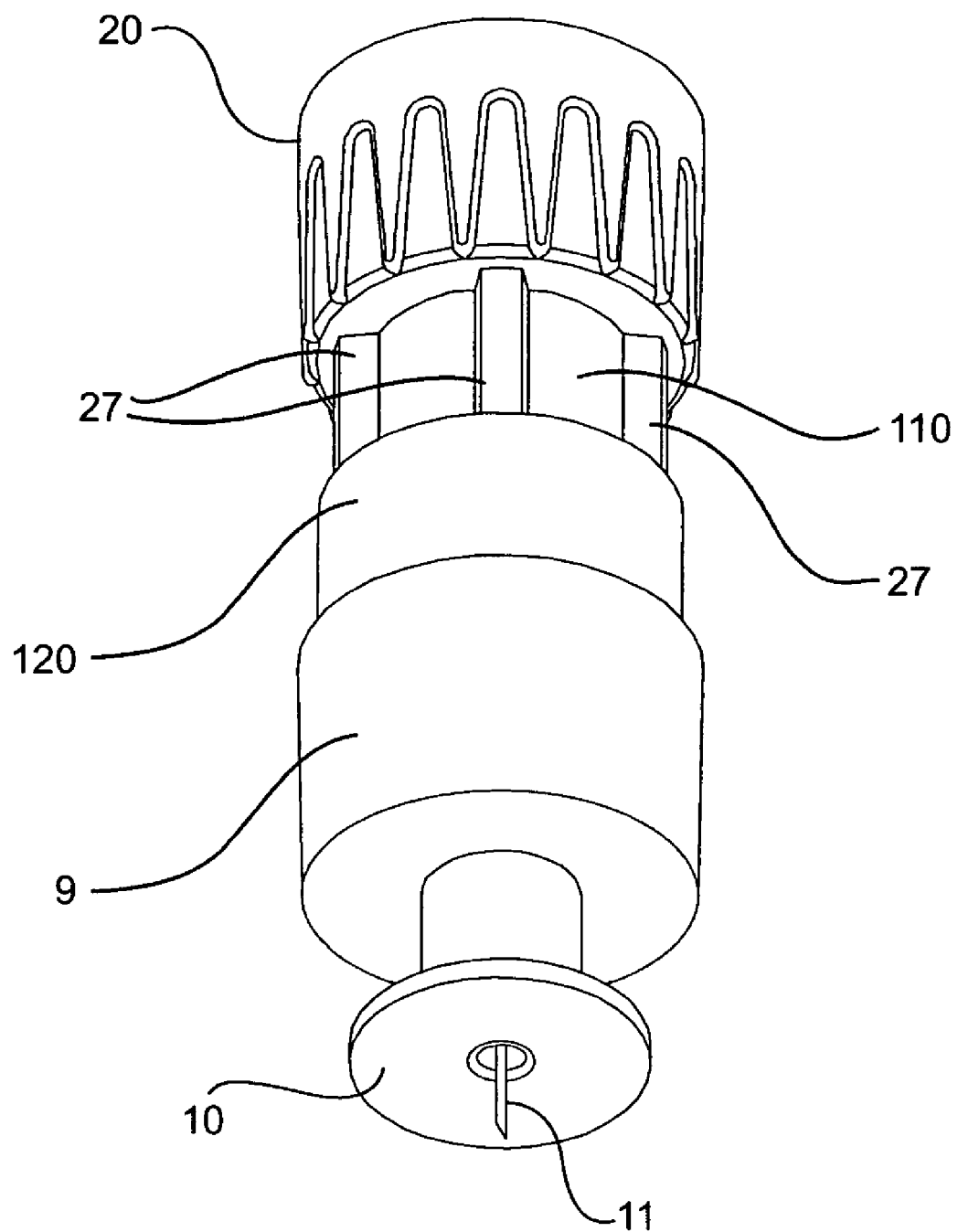
FIG. 10 is a view of an exemplary needle stop and a pen needle/reservoir assembly according to an embodiment of the present invention.

A more detailed description of the reservoir housing 20 will now be made with reference to FIG. 5. The reservoir housing 20 comprises an upper sleeve 130 and pen needle connecting portion 6. The upper sleeve 130 and the pen needle connecting portion 6 are slidably connected to one another. The upper sleeve 130 comprises the primary reservoir 1, septum penetrating cannula 4, medial wall 140, internal screw threads 17, check valve 3, secondary reservoir wall 110 and travel limits 5a. The pen connecting portion 6 comprises front sleeve 120, which forms the upper exterior wall of the pen connecting portion 6, screw threads 17a, center channel 90, travel limits 5b and sliding seal 8, which is affixed to the base of pen connecting portion 6. The secondary reservoir wall 110 of the upper sleeve 130 slidably fits into pen connecting portion 6 between the front sleeve 120 and the sliding seal 8. The travel limits 5a and 5b of the respective components prevent the upper sleeve and the pen connecting portion from sliding apart. The volume of the secondary reservoir 2 expands to a fully filled state when the travel limits 5a and 5b of the upper sleeve 130 and pen connecting portion 6, respectively, contact one another and contracts as the travel limits 5a and 5b move further apart. The upper sleeve 130 and the pen needle connecting portion 6 is depicted with the secondary reservoir wall 110 and the guide ribs 27 (shown in FIG. 4 and FIG. 10) with the secondary reservoir 2 in a dosed state, and the check valve 3 substantially open.

Referring to FIG. 6, the medicament cartridge 12 is typically a glass tube sealed at one end with the septum 16 and sealed at the other end with the stopper 15. The septum 16 is pierceable by the septum penetrating cannula 4, but does not move with respect to the medicament cartridge 12. The plunger or stopper 15 is axially displaceable within the medicament cartridge 12 while maintaining a fluid tight seal. The injection device 100 further comprises a dose setting mechanism, such as the dose knob/button 24 and the outer sleeve 13 (shown in FIG. 1) having the lead screw or rod 7 (shown in FIG. 2) and plunger 15. Once assembled, the reservoir housing 20 is slidingly disposed with respect to the outer sleeve 13.

The check valve 3 is disposed on the medial wall 140 to control flow of medicament between the primary reservoir 1 and the secondary reservoir 2. The check valve 3 permits flow of medicament from the primary reservoir 1 to the secondary reservoir 2, but prevents flow from the secondary reservoir 2 back to the primary reservoir 1. It is noted that the injection device 100 may be designed such that the check valve 3 is not required. Specifically, the injection device 100 may be such that the backpressure from the tissue space is never enough to overcome the internal resistance provided by the dose setting mechanism and other components of the injection device 100. Consequently, the backpressure cannot force medicament back into the primary reservoir 1.

The septum penetrating cannula 4 is mounted to the medial wall 140 and disposed proximate to the check valve 3. The septum penetrating cannula 4 is positioned so that, when the medicament cartridge 12 is inserted into the primary reservoir 1, the cannula 4 penetrates the end of the medicament cartridge 12, opening a flow path from the medicament cartridge 12, through the septum penetrating cannula 4, through the check valve 3 and into the secondary reservoir 2.

The distal end of the reservoir housing 20 is slidingly disposed within the front sleeve 120. Preferably, flanges are integrally formed on the distal end of the housing 20 to form the axial travel limit 5a. The proximal end of the front sleeve 120 is also flanged to form the axial travel limit 5b of the pen needle connecting portion 6. The travel limits 5a and 5b cooperate by intersecting to restrict the relative axial displacement of the housing 20 and the front sleeve 120. As discussed below, this cooperation between the travel limits 5a and 5b controls the volume of medicament delivered in a single stroke.

The front sleeve 120 comprises the pen needle connecting portion 6 at its distal end, the travel limits 5b and sliding seal 8. The travel limits 5b are preferably 90 degree flanges on the exterior walls of the front sleeve 120. The sliding seal 8 is fixedly attached to the pen needle connecting portion 6. The central opening 90, which accepts the distal end of the patient needle 11, extends through the sliding seal 8. The proximal end of the sliding seal 8 is slidingly disposed within the secondary reservoir 2 of the reservoir housing 20, while the exterior walls of secondary reservoir 2, which comprise travel limits 5a, fit between the exterior walls of the front sleeve 120 and the sliding seal 8.

When ready for injection, the pen needle assembly 9 is attached to the pen needle connection portion 6, such as by threading or other techniques known in the art. The pen needle assembly 9 comprises the patient needle 11 and needle stop 10. Once attached, the patient needle 11 is in fluid communication with the secondary reservoir 2 above the sliding7 seal 8 via the central opening 90. The needle stop 10 may be affixed to the pen needle assembly 9 to control the exposed length of the patient needle 11 available for insertion into tissue, thereby controlling the depth of delivery.

The parts that comprise the injection mechanism 100 (with the exception of the patient needle 11 and the septum penetrating cannula 4) are preferably made from plastic through an injection molding process or other suitable materials and processes. The patient needle 11 and septum penetrating cannula 4 may be made of surgical-quality metals, such as stainless steel. The primary reservoir 1 and the secondary reservoir 2 are preferably defined by a single molded piece but, it will be appreciated, that separate parts could be formed and then connected to create the appropriate structure. The septum penetrating cannula 4 and check valve 3 may be secured in place in the housing by snap-fitting, interference-fitting, adhesives, welding or other such methods or means of affixation.

The medicament cartridge 12, containing a predetermined amount of medicament, is first attached to the pen injector device 100, in a manner known and understood in the prior art of pen injector devices. In operation, the primary reservoir 1 would be attached to threads 17 on the distal end of the medicament cartridge 12, shown in FIG. 6. Threads at the distal end of the medicament cartridge 12 may engage the threads 17 within the housing 20 comprising the primary reservoir 1. Other means of engaging the medicament cartridge 12 to the housing 20 may be used. As the medicament cartridge 12 is being inserted into the primary reservoir 1, the septum penetrating cannula 4 penetrates the septum 16 of the medicament cartridge 12, creating a flow path from the interior of the medicament cartridge 12 through the septum penetrating cannula 4 and the check valve 3 to the secondary reservoir 2. An embodiment of the invention comprising the reservoir housing 20, the front sleeve 120, the secondary reservoir wall 110, the sliding seal 8, the pen needle assembly 9, the needle stop 10 and the patient needle 11 is depicted in FIG. 6 with the secondary reservoir 2 in a fully collapsed, pre-dosed state.

Figure 7:
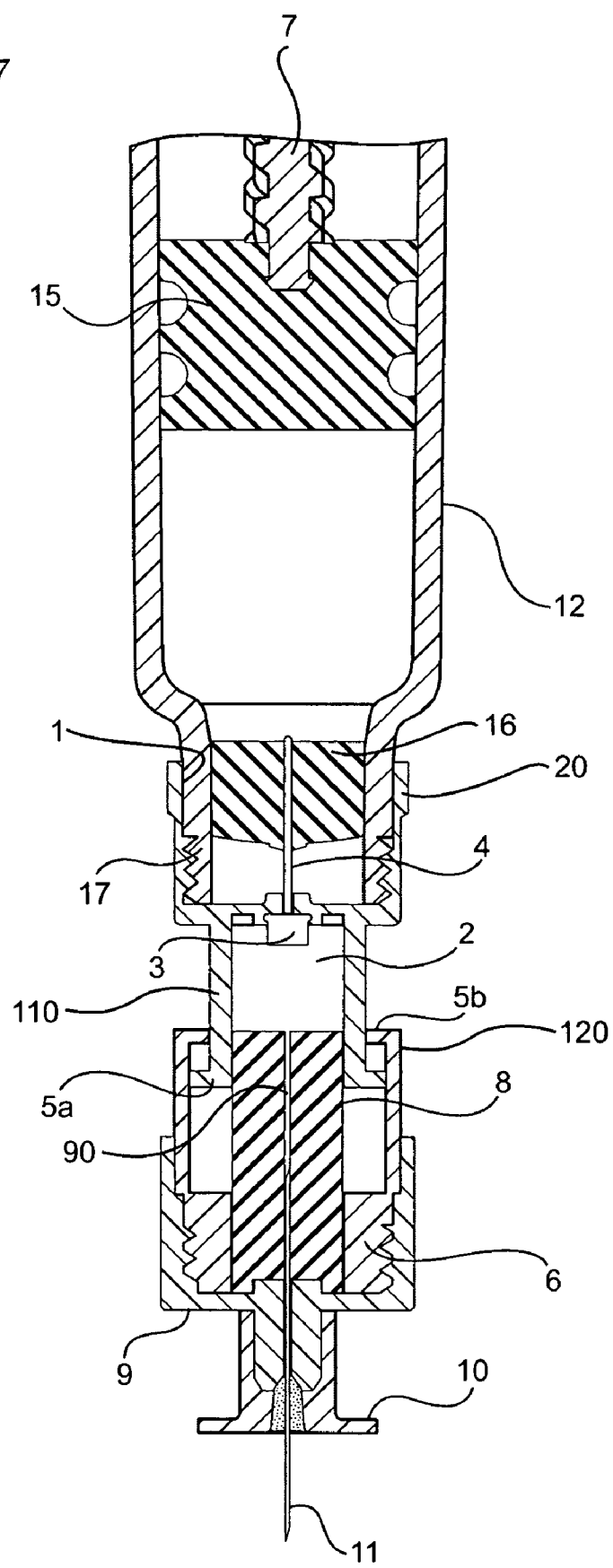
FIG. 7 is a view of the injector device in a dosed and loaded state according to an embodiment of the present invention.

The user then selects the amount of medicament to be delivered. This is achieved by turning the knob or dial 24 on the dose setting mechanism, or other methods traditionally employed in connection with pen injection devices to limit the stroke of the lead screw 7 and stopper 15. The user then advances the dial/dose knob 24, toward the pen needle assembly 9. The relative movement of the dial/dose knob 24 causes the lead screw 7 and stopper 5 to move toward the pen needle assembly 9. The stopper 15, which abuts the lead screw 7, passes through the primary reservoir 1, which is filled by the medicament cartridge 12, effectively collapsing the primary reservoir 1 a selected amount. This "loading stroke" drives medicament from the primary reservoir 1 to the secondary reservoir 2. During the loading stroke, it may be desirable to invert the device (such that the pen needle is pointing up) to discourage pre-injection leakage. Since there is no backpressure, a relatively small amount of force is required to drive the medicament into the secondary reservoir 2. The injection device 100 is now in the state shown in FIG. 7. An embodiment of the invention comprising the reservoir housing 20, the front sleeve 120, the secondary reservoir wall 110, the sliding seal 8, the pen needle assembly 9, the needle stop 10 and the patient needle 11 is depicted in FIG. 7 with the secondary reservoir 2 in a dosed state and the check valve 3 in a substantially open state.

Figure 8:
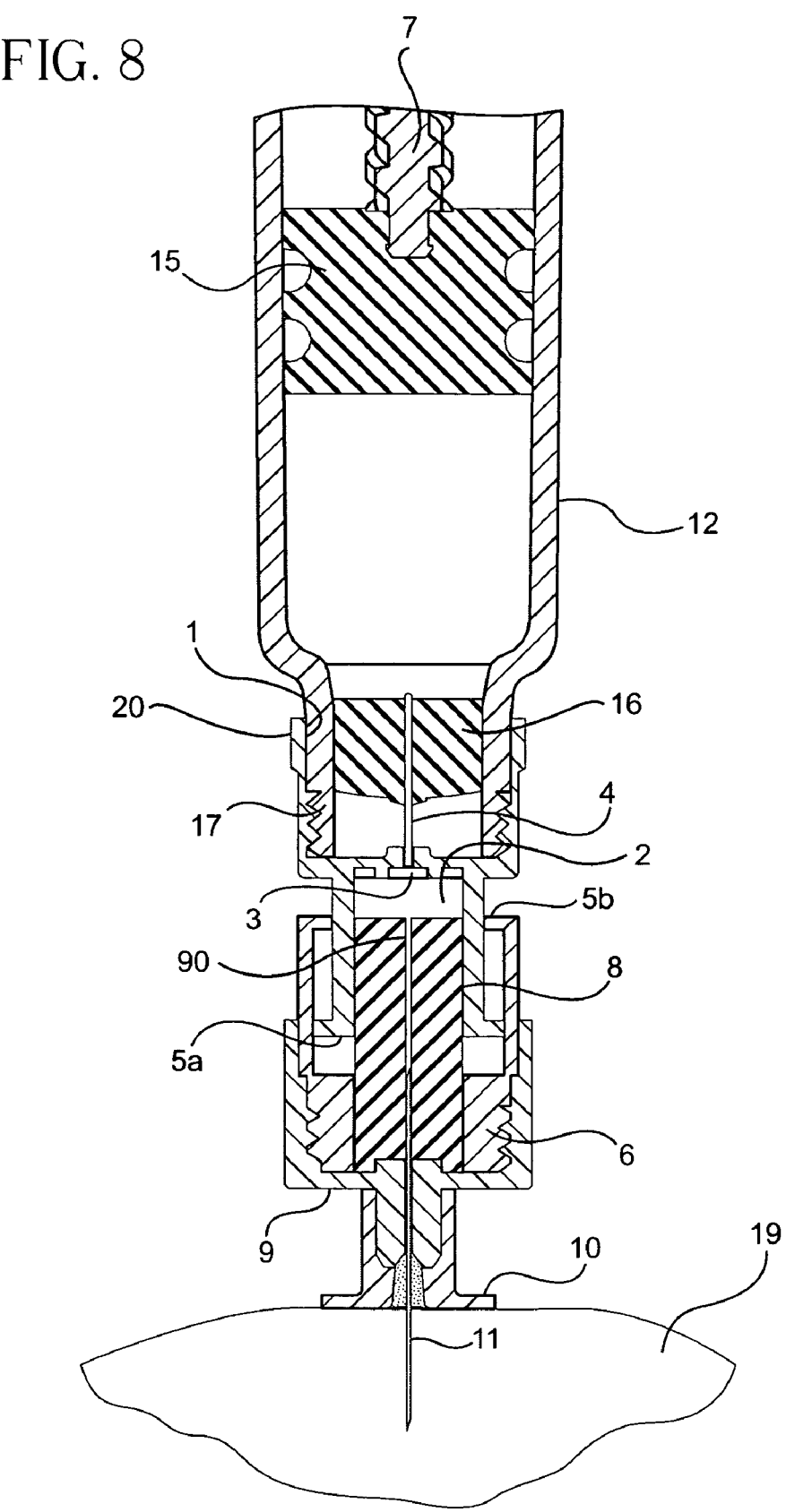
FIG. 8 is a view of the injector device penetrating the skin into a targeted tissue layer according to an embodiment of the present invention.

As shown in FIG. 8, the injection device is now placed on a patient's skin surface 19 such that the needle is fully seated into the tissue, with secondary reservoir partially closed, and medicament shown being delivered to the intradermal space or other designated tissue space. The patient needle 11 is inserted into the skin up to the needle stop 10. For certain applications, the needle stop 10 is designed such that the exposed length of the needle is between 0.2 mm and 5.0 mm and the outlet of the patient needle 11 is disposed within the intradermal layer or shallow subcutaneous layer of the skin. It will be appreciated that the patient needle 11 length and the needle gauge can be modified to access different tissue layers (or multiple tissue layers), depending on the particular application.

Once the needle stop 10 is seated on the skin, a downward force is applied to the injector device by grasping the outer sleeve 13 of the injector device (see outer sleeve 13 as depicted in FIG. 1). The force exerted on the outer sleeve 13 is translated, via the medicament cartridge 12. The medicament cartridge 12 subsequently drives the housing 20 toward the pen needle connecting portion 6. This movement causes axial movement of the sliding seal 8 within the secondary reservoir 2 towards the medial wall 140, thus, collapsing the volume of the secondary reservoir 2 and causing the check valve 3 to seal the pathway between the primary reservoir 1 and the secondary reservoir 2. In the process of collapsing the volume of the secondary reservoir 2, the pen injection device 100 is pressurizing the medicament in the secondary reservoir 2, thereby driving it through the patient needle 11, into the patient's tissue. The guide ribs 27 located on the outside of the secondary reservoir wall 110 and the axial travel limits 5a and 5b provide alignment for the co-axial movement between the front sleeve 120, the sliding seal 8 and secondary reservoir 2 to help ensure that the benefits of the mechanical advantage provided by embodiments of the invention are fully translated and achieved. An embodiment of the invention comprising the reservoir housing 20, the front sleeve 120, the secondary reservoir wall 110, the sliding seal 8, the pen needle assembly 9, the needle stop 10, the patient needle 11 and the guide ribs 27 (shown in FIG. 4 and FIG. 10) is depicted in FIG. 8 with the check valve 3 sealing the primary reservoir 1 and the collapsing of the secondary reservoir 2 to evacuate a medicament into the targeted tissue space.

As shown in FIG. 8, the primary reservoir 1 and the secondary reservoir 2 each have cross sectional areas that are designed to achieve certain delivery characteristics. Specifically, in certain applications, it is desirable to facilitate creating greater fluid pressure in the secondary reservoir 2 without increasing the actuation force. In such cases, the cross sectional area of the secondary reservoir 2 (taken through section AA as shown in FIG. 5) is less than the cross sectional area of the primary reservoir (taken through section BB as shown in FIG. 5). Since the cross sectional areas depicted by section AA of the secondary reservoir 2 and section BB of sliding seal 8 are relatively small, only minimal actuation forces are required to achieve the increase fluid pressures necessary for delivery, even into the intradermal tissue space.

Figure 9:
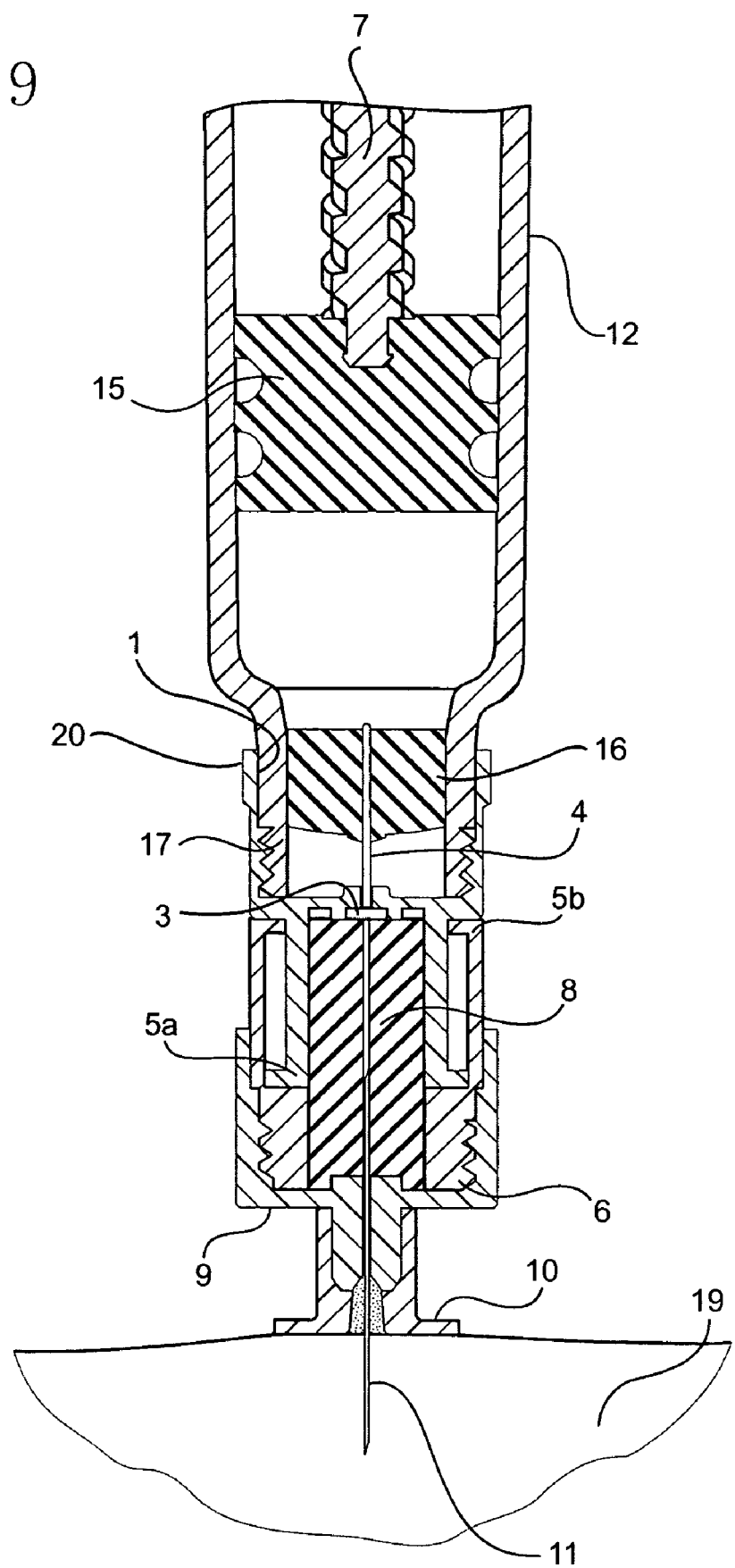
FIG. 9 is a view of the injector device fully penetrating and positioned on the skin in the post injection state according to an embodiment of the present invention.

FIG. 9 shows the injection device 100 according to an embodiment of the present invention in the post-injection state. The medicament has been completely evacuated from the secondary reservoir 2 due to the collapse of the volume of the secondary reservoir 2 and the axial travel limits 5a and 5b are at the end of their internal and external travel limits, respectively. This travel limitation corresponds with the sliding seal 8 being located at the extreme distal end of the secondary reservoir 2 against the closed check valve 3, if present. The injection device 100 can now be removed from the skin.

The axial travel limits 5a are stopped by axial travel limits 5b that are integral to the top of the pen needle connecting portion 6. The axial travel limits 5b are also preferably flanges with a 90 degree angle that intersect with axial travel limits 5a to prevent further expansion of the volume of the secondary reservoir 2. The designs of the axial travel limits 5a and 5b are only exemplary and other configurations achieving the same results may be substituted for these exemplary designs. For instance, a frictional element or spring-loaded mechanism could be employed between the axial travel limits 5a and 5b to maintain the secondary reservoir 2 at intermediate positions there between.

The pen needle connecting portion 6 may have molded into its internal sides sliding seal guides (not shown), which in cooperation with guide ribs 27 serve to maintain the alignment of the sliding seal 8. This embodiment of the invention depicts a mating seal configuration which can be dictated by the specific guidance and design requirements of the invention. The needle stop 10 and the patient needle 11 are preferably removably connected to pen needle assembly 9. The pen needle assembly 9 will be described later in more detail below with respect to FIG. 10.

The depth of the injection is primarily determined by the length of the patient needle 11 that is left protruding from the needle stop 10 as the two are affixed to the pen needle assembly 9. A representative needle stop 10 and patient needle 11 integral to the pen needle assembly 9 are shown for reference purposes in FIG. 10. The diameter and geometry of the needle stop 10 may have an effect on the specific injection force and injection pressure ratio required for intradermal medicament delivery since excessive force against the needle stop 10 at the site of the injection may result in discomfort to the user as well as additional localized compression of the intradermal tissue layer, which further increases tissue backpressure due to resistance within the intradermal tissue layer. The pen needle assembly 9 may comprise a threaded interior to facilitate attachment to an injection device, in particular, to the pen injection device 100. Additionally, the removal of the pen needle assembly 9 may also allow the discarding of the used needle for safety and sanitary considerations. In other embodiments, the needle stop 10 and patient needle 11 may be attached to the pen needle assembly 9 by a threaded or other suitable connection means, and the two can be discarded instead of the entire pen needle assembly 9. Sliding seal guide ribs 27 are positioned on the exterior of the secondary reservoir wall 110 and serve to maintain the alignment of the front sleeve 120 with the reservoir housing 20 as the sliding seal 8 and secondary reservoir wall 110 move within the front sleeve 120. Additional embodiments can include the pen needle assembly 9, pen needle connecting portion 6 and the upper sleeve 130 (see FIG. 10) as a single disposable unit.

Figure 11:
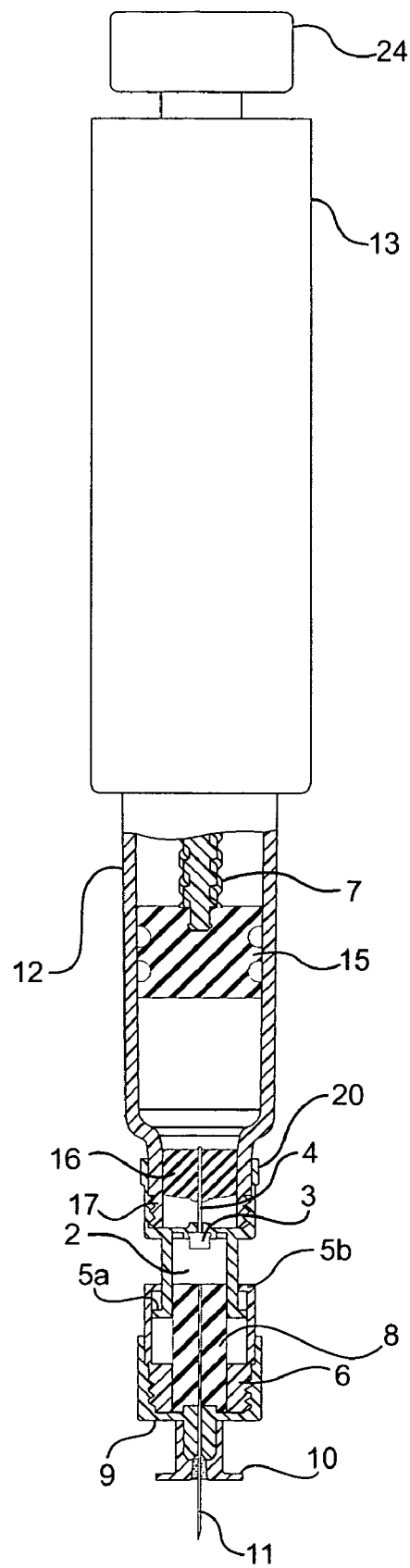
FIG. 11 is a view of an exemplary pen injection device with a cross-sectional view of an empty secondary reservoir according to an embodiment of the present invention.

A preferred embodiment for the injection device 100 is a pen-type injector device as shown in FIG. 11. The pen injector device 100, as shown in FIG. 11, is in a substantially open, dosed state ready to deliver the medicament into the intradermal tissue space. In FIG. 11, the partial amount of medicament, within the volume accepted by the secondary reservoir 2 has been metered and transferred using the dose knob/button 24 from the medicament cartridge 12 through the septum penetrating cannula 4 and check valve 3 into the secondary reservoir 2. The displacement of medicament is evidenced by the location of the sliding seal 8 with respect to the distal wall and optional check valve 3 and by the medicament filling the secondary reservoir 2. The sliding seal 8 displaces and the check valve 3 opens as the medicament fills the secondary reservoir 2, along with the pen needle connecting portion 6 and the attached pen needle assembly 9 including the needle stop 10 and patient needle 11.

Figure 12:
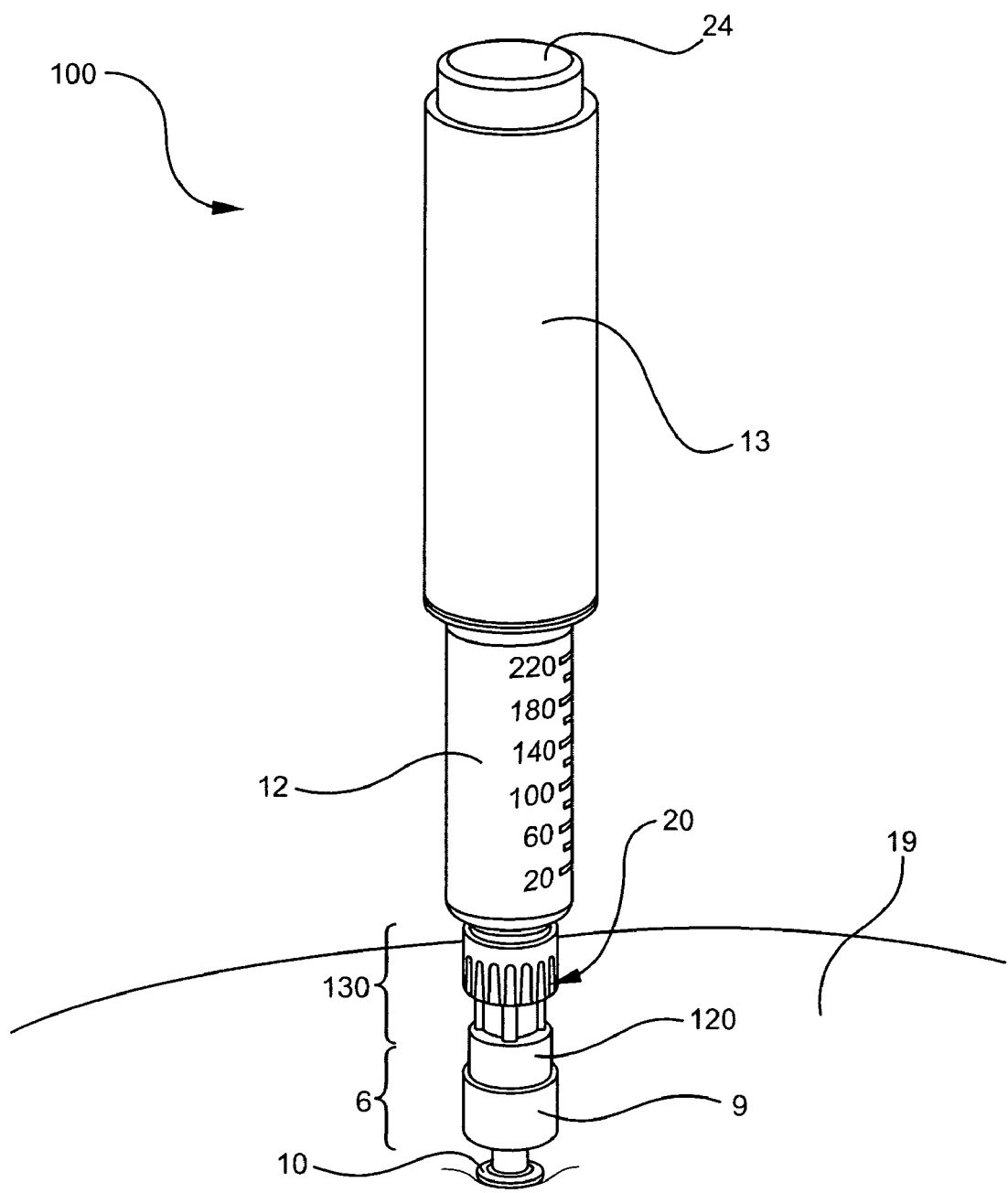
FIG. 12 shows a full view with the needle stop pressed against the skin and the patient needle penetrating the skin into a tissue layer according to an embodiment of the present invention.

An exemplary pen-type injector device desirable for use in connection with the injection mechanism discussed above is shown in FIG. 12 in a substantially open, dosed position ready to administer an injection to a patient after the dosage of medication has been dispensed and transferred to the secondary reservoir 2 using the dosage knob/button 24. The pen-type injector device 100 is depicted with the needle stop 10 pressed against the skin 19 and the patient needle 11 (not shown) penetrating the skin 19 into the intradermal tissue layer. The skin 19 can be seen bowing below and around the needle stop due to the force applied. With the pen-type injector device 100 ready to deliver the medicament into the intradermal layer, a downward force applied to the injector device 100 when grasped at the outer sleeve 13 is translated to the medicament cartridge 12. This force is translated to the reservoir housing 20, which comprises the primary reservoir 1, the secondary reservoir 2, the check valve 3, the septum penetrating cannula 4, and the axial travel limits 5a. The medicament cartridge is fastened to the reservoir housing 20 through the integral internal threads 17 within the primary reservoir 1. The force being applied through the outer sleeve 13 is then translated back from the skin through the needle stop 10 and acts to facilitate the movement of the upper sleeve 130 in relation to the pen needle connecting portion 6. This application of force causes the movement of the sliding seal 8 and closure of the check valve 3, inside the secondary reservoir 2, which in turn facilitates the expulsion of the medicament from the secondary reservoir 2, as contained within the secondary reservoir wall 110, causing the delivery of the medicament through both the central opening 90 in the sliding seal 8 and patient needle 11 (not shown) preferably into the targeted tissue layer.

Figure 13:
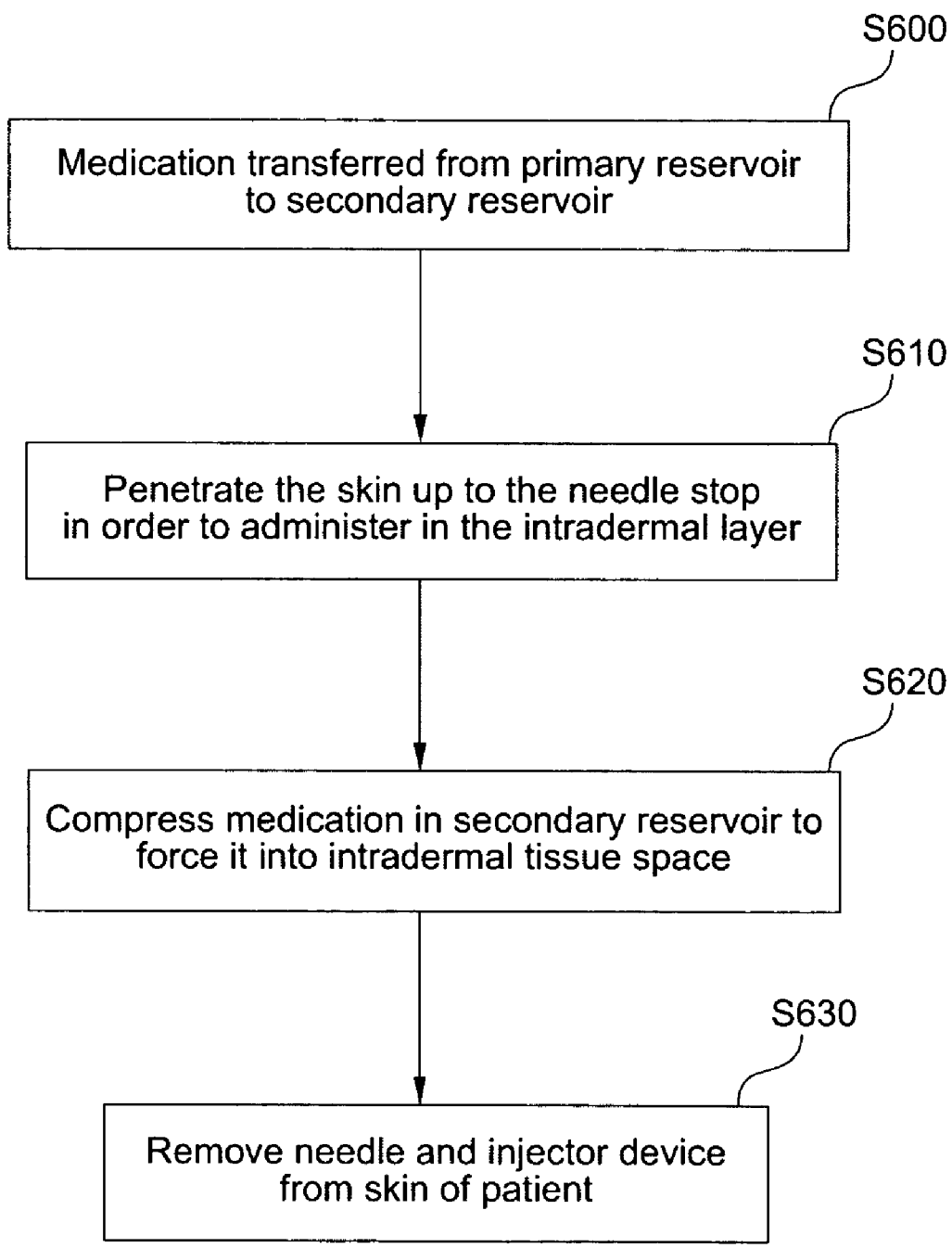
FIG. 13 is a flowchart depicting the steps involved in administering an injection according to an embodiment of the present invention.

The preferred method for using the injection device is illustrated in FIG. 13. In step (S600), the medication is transferred from the medicament cartridge 12, which is held in the primary reservoir 1, into the secondary reservoir 2. To transfer the medication, the user preferably meters in the desired measured dosage of medication using the dosage knob/button 24, which will fill the secondary reservoir with the desired dosage either directly or through subsequent depression of the dosage knob/button 24. The check valve 3, if necessary, prevents the medication from flowing back into the primary reservoir 1 from the secondary reservoir 2. Upon filling the secondary reservoir 2, the injection device 100 is now ready to be inserted into the skin of the patient. The skin 19 is penetrated by the patient needle 11, which is inserted up to the needle stop 10, and the patient needle 11 is in the intradermal layer of the patient's skin 19 in step (S610). The user then applies a relatively low force (substantially the same force as that required to inject medication into the subcutaneous tissue space) to expel the medication from the secondary reservoir 2 causing the medication to be injected into the intradermal layer of the skin 19 at a higher pressure due to the mechanical advantage provided by the reduced cross-sectional area of the secondary reservoir 2 in step (S620). Upon administering the dosage of medication, the user removes the patient needle 11 and injection device 100 from the skin 19 of the patient in step (S630).

A visual and/or audible indicator may be incorporated into the pen injector device 100 when the full volume of medicament in the secondary reservoir 2 has been dispensed. An indicator may serve to alert the user or patient as to when an adequate amount of actuation force has been applied to the pen injector device 100 and consequently to the skin 19 surface, thereby delivering the injection dose while minimizing the discomfort at the injection site associated with applying unnecessary excess force. An indicator may also aid the user and patient as a helpful tool in determining when an adequate amount of time has passed to allow for full administration and absorption of the medicament into the intradermal layer. The audible indicator may utilize the friction between two moving parts of the injector pen device 100 to produce a signal.

An embodiment of the present invention has been shown to be integrated into a reservoir housing comprising both the primary reservoir 1 and the secondary reservoir 2. However, other embodiments of the present invention can be integral to the pen injector device, integral to the patient needle assembly, integral to the medicament reservoir and cartridge, or provided as a discrete module that is added to an existing pen injector device or any of the other subcomponents mentioned above. Embodiments of the present invention can be designed such that aspects of the invention can be tailored for the end-user in relation to the specific characteristics of the medicament being administered, e.g., viscosity, the specific characteristics of the body space being administered to, e.g., intradermal, and/or the specific characteristics of the end user or patient, e.g., age. Additionally, the shape and size of the primary reservoir 1, secondary reservoir 2 and the sliding seal 8 can each vary independently or in combination as dictated by the injection pressures required by the specific applications of the invention. Additionally, the surfaces of the secondary reservoir 2 and the sliding seal 8 that are in contact with the fluid for injection may also be shaped differently.

In certain embodiments, the secondary reservoir 2 may also comprise a permanent, integral component subsystem of an intradermal pen injector device, an integral component or feature of a disposable intradermal pen needle that is discarded after each use, an integral component or subsystem of the primary medicament reservoir or cartridge discarded after the medicament has been fully discharged, or as a discreet component or subsystem that may be added to a pen or syringe injector system when higher injection pressures are required.

The size or the effective volume of the secondary reservoir 2 may be varied by altering its cross-sectional area and or the length. Additionally, the secondary reservoir 2 may also have an unconventional shape such as a hollow-cylindrical spring shape or the like. Alternative embodiments of the present invention may be better suited as disposable (one time use) devices while other embodiments may be better suited as re-usable devices based on factors such as manufacturing processes, robustness of design or cost considerations.

Additionally, it is envisioned that the secondary reservoir 2 may have a larger cross-sectional area through section AA than the cross-sectional area of the primary reservoir 1 taken through section BB shown in FIG. 5, whenever a reduced mechanical advantage is necessary for a customized tactile response while injecting. In such cases, the pen needle connecting portion 6 and the sliding seal 8 would be of a larger cross-sectional area AA than cross-sectional area BB.

Use of the secondary reservoir 2 including the check valve 3 will also reduce the effect of "drooling" or "weeping" when the needle is removed from the patient due to compliance of either the medicament cartridge 12, the plunger 15, leadscrew 7, the septum 16, or all of these components combined as is typical of prior art injection devices. The secondary reservoir 2, when used with the check valve 3, prevents the medicament cartridge 12 or other medication dispenser devices from experiencing the backpressure of the fluid in the secondary reservoir 2 as it is injected into a patient or user. Therefore, the plunger or stopper 15, leadscrew 7 or the septum 16 does not experience the pressures associated with the injection of fluids because of the check valve 3 and accordingly, do not need to return to their original shape after being pressurized, which limits the amount of delivery mechanism compliance within the pen injection device.

The reduced or increased cross-sectional area secondary reservoir 2 may be incorporated onto standard pen injector devices, or other types of delivery or injection devices, not limited to medicament delivery or usage in a medical device, employing a chamber or reservoir or cartridge for the purpose of dispensing of medicaments or other types of liquids for any end purpose requiring the application of force to administer an injection. Additionally, embodiments of the present invention may also be used to inject medication or other fluids into areas other than only the intradermal tissue layer. For instance, embodiments of the present invention can be used by persons, who are not capable of producing enough force to give themselves injections, to enable them to give themselves injections into at least the subcutaneous space.

In order to overcome the high backpressures associated with injecting fluids, such as medications, into the intradermal tissue layer, a greater amount of actuator force must be applied to the fluid to create greater fluid pressure. Equation 1 describes the relationship between the force applied by a user of a syringe or pen and the area of the plunger passing through the reservoir or medicament cartridge to create the greater fluid pressure. As related to the embodiments of an intradermal pen injector device, for instance, a smaller diameter fluid reservoir and associated plunger or stopper will facilitate higher delivery fluid pressures than a larger diameter fluid reservoir and its plunger under the same amount of actuation force applied by the user or patient.

Pressure=(user applied actuation force)/(area of plunger)     Equation 1

Table 1 below illustrates the impact of a secondary reservoir with a reduced cross-sectional area according to embodiments of the present invention through the following example. A $5^{th}$ percentile female, who is a female who represents the physical neuromuscular characteristics of 5 percent of the overall female population, can push with her thumb just under 1 pound of force. Thus using a standard pen injector device with a plunger having a cross-sectional area measured at 0.1134 in$^2$., she can inject fluid at approximately 9 pounds per square inch (psi). This low pressure would typically be insufficient to inject into the dense intradermal tissue layer at a reasonable rate for commercially viable medicament delivery. It is estimated that it would take approximately 1½ minutes to inject approximately 30 units of insulin at this pressure. However, the same $5^{th}$ percentile female, using a pen injector device incorporating a secondary reservoir with a plunger having a cross-sectional area measured at 0.0314 in$^2$, would be capable of injecting fluid at approximately 31 psi. This higher fluid pressure generated from the same amount of actuation force would be better suited to inject into the dense intradermal tissue layer at a reasonable rate for medicament delivery that would be more commercially viable. Therefore, the same user could inject approximately 30 units in less than thirty seconds due to the increased mechanical advantage provided by the application of force to the reduced cross-sectional area of the secondary reservoir. In general, as the plunger surface area decreases, an additional mechanical advantage would be available to the end user, who applies the same amount of actuation force, to enable increased injection pressures.

TABLE 1

Example of Theoretical Model Demonstrating Mechanical Advantage Afforded by Embodiments of the Invention

| | Pressures Generated | | | |
|---|---|---|---|---|
| | Pressure (PSI) | Plunger Diameter (in) | Area (in$^2$) | Actuator Force (lbs) |
| Conventional Pen | 8.527 | 0.3800 | 0.1134 | 0.9670 |
| Secondary Reservoir | 30.796 | 0.2000 | 0.0314 | 0.9670 |

As shown in the Table 1 above, applying actuation force to a plunger with a smaller cross-sectional area, such as the sliding seal 8 in the secondary reservoir, creates greater injection delivery pressure on the fluid. Throughout the specification, the cross-sectional area will be the area that is used to apply pressure to the fluid as it is injected as shown by cross-section AA in FIG. 5. This force may be applied by a plunger, a mechanism within the injection device, such as the sliding seal 8, or some other suitable actuating means.

This additional mechanical advantage resulting from the use of the secondary reservoir 2 with a reduced cross-sectional area not only allows for injections into the intradermal tissue layer, but also provides advantages for injecting fluid into other spaces by those users not capable of producing enough force to perform even subcutaneous injections, such as the elderly, people with arthritis or diabetics with nerve damage/neuropathy.

In addition to providing acceptable injection pressures into the intradermal tissue layer, embodiments of the invention can contribute to the delivery of medication at a more controlled rate of injection. When injection pressures applied are in excess of the intradermal layer's, or receiving tissues', ability to accept the medicament, the delivered medicament may "jet" past the desired tissue depth. It may be desirable that medications be delivered at a specific depth, but also at a more controlled rate of injection, which is another means to help achieve depth accuracy of medicament delivery, thereby preventing the medicament from "jetting" back out through the skin or from being delivered below the desired tissue depth (typically, the intradermal layer). By incorporating the secondary reservoir 2 in-line or in series with the injection mechanism portion of the pen injector device 100, it contributes to achieving a more controlled rate of injection of medicament by maintaining the actuation force at a familiar level throughout the injection process. As depicted in the figures, the primary reservoir and secondary reservoir 2 are located co-axially.

Using the mechanical advantage of the reduced cross-sectional area secondary reservoir 2, the user is able to concentrate on applying familiar and uniform actuation forces to inject medication instead of having to exert the greater actuation forces necessary to overcome the backpressure created by the targeted tissue layer. Despite the variability of both injection forces, as applied by users and patients, and the backpressures applied by the patient's intradermal tissue, a number of known factors also help contribute to providing a more controlled rate of delivery, such as: the specific diameter or cross-sectional area, and length (known volume) of the secondary reservoir 2, the diameter of the plunger or sliding seal 8, the cross-sectional area of the plunger or sliding seal 8, the characteristics of the medicament (such as viscosity, density), and the gauge of the patient needle 11. The presence of resistance due to backpressure and a reduced mechanical advantage during injection will allow the user to visually note the injection of the medication while also being provided with physical tactile feedback as the medication is injected. The secondary reservoir 2 may be tailored to the type of medicament to be delivered, the desired delivery depth, the relative tissue density of the intradermal tissue space depending on patient demographics and body site location, the needle gauge and effective length to help prevent the jetting phenomenon.

Although injections into the intradermal tissue layer have been primarily described, the embodiments of the instant invention may also be used for injections into other types of organs, tissues, both human and non-human, or body masses, such as fluid implants and the like.

The exemplary embodiments have been described with respect to a pen-type injector and a primary and secondary reservoir, but one of ordinary skill may envision alternative embodiments without departing from the scope of the present invention.

We claim:

1. An injection mechanism for injecting fluid into a targeted tissue layer comprising:
    a primary reservoir for storing fluid prior to injection having a first axis;
    a secondary reservoir for holding the amount of fluid to be injected having a second axis, wherein the secondary reservoir is located co-axially and in series with the primary reservoir and has a smaller cross-sectional area than the cross-sectional area of the primary reservoir;
    a needle connecting portion comprising a sliding seal, a needle assembly, and a needle stop, wherein the sliding seal comprises a needle septum forming one side of the secondary reservoir and through which the fluid to be injected passes from the collapsing secondary reservoir during the injection; and
    a patient needle for intersecting the needle septum of the sliding seal, and for penetrating the skin of the patient to inject the fluid in the targeted tissue layer.

2. The injection mechanism of claim 1, wherein said patient needle has an exposed length of between approximately 0.5 mm and approximately 5 mm.

3. The injection mechanism of claim 1, wherein said patient needle has an exposed length of between approximately 0.5 mm and approximately 3.5 mm.

4. The injection mechanism of claim 1, wherein said patient needle has an exposed length of between approximately 1.5 mm and approximately 3.0 mm.

5. The injection mechanism of claim 1, wherein said patient needle delivers fluid in the intradermal or the shallow subcutaneous tissue space.

6. The injection mechanism of claim 1, further comprising:
    a check valve located between the primary and secondary reservoirs for preventing fluid from leaking from the secondary reservoir back into the primary reservoir or medicament cartridge.

7. The injection mechanism of claim 1, wherein said secondary reservoir is filled with fluid causing said sliding seal to move proximal in said secondary reservoir.

8. The injection mechanism of claim 1, wherein the patient needle penetrates said patient skin until stopped by the needle stop, wherein said needle stop has an area larger than that of said patient needle.

9. The injection mechanism of claim 8, wherein an injection is administered by applying pressure to said primary reservoir thereby causing said fluid in said secondary reservoir to flow through said needle septum and patient needle to be injected into said intradermal tissue.

10. A method for injecting fluid into an intradermal tissue layer of a patient comprising the steps of:
    transferring fluid from a primary reservoir with a first cross-sectional area into a secondary reservoir having a second cross-sectional area less than that of said first cross-sectional area;
    preventing said fluid from flowing from the secondary reservoir back into the primary reservoir; and
    pressurizing the fluid in said secondary reservoir to force it into said intradermal tissue layer of a patient.

11. The method of claim 10, further comprising the step of:
    penetrating the skin of said patient with a needle in fluid communication with said secondary reservoir prior to said pressurizing step.

12. The method of claim 10, wherein the transferring step comprises turning a dosage knob to set the amount of fluid in the primary reservoir that is transferred to said secondary reservoir.

13. The method of claim 10, wherein said preventing step comprises using a check valve, wherein said check valve allows fluid to flow from the primary reservoir to the secondary reservoir and prevents the medication from substantially flowing from the secondary reservoir back into the primary reservoir.

14. The method according to claim 11, wherein the penetrating step comprises limiting the depth that the needle penetrates into the skin.

15. The method of claim 14, wherein the depth that the needle penetrates into the skin is limited by a needle stop.

16. An apparatus for delivery of compounds to the intradermal tissue of a patient's skin, the apparatus comprising:
    a reservoir housing having a distal end and a proximal end, and defining a primary reservoir, and a secondary reservoir in fluid communication;
    a pen needle assembly mounted to the distal end of the reservoir housing;
    a needle securely mounted to the pen needle assembly in fluid communication with the secondary reservoir and extending distally from the pen needle assembly; and
    a needle stop having a skin-engaging surface disposed in a preselected position with respect to the pen needle assembly such that a preselected portion of the needle extends distally from the skin-engaging surface;
    wherein the reservoir housing further comprises a lower sleeve slidingly engaged to an upper sleeve, and movable from a first position to a second position during injection; and
    wherein, when the lower sleeve is in the first position, the secondary reservoir has a first volume and when the lower sleeve is in the second position, the secondary reservoir has a second volume, and wherein the second volume is less than the first volume.

17. The apparatus of claim 16, wherein the pen needle assembly is selectively and directly mounted to the reservoir housing.

18. The apparatus of claim 16, wherein the pen needle assembly is fixedly mounted to the reservoir housing.

19. The apparatus of claim 16, wherein the needle stop is integrally formed with either the pen needle assembly or the reservoir housing.

20. An apparatus for delivery of compounds to the intradermal tissue of a patient's skin, the apparatus comprising:
    a reservoir housing having a distal end and a proximal end, and defining a primary reservoir, and a secondary reservoir in fluid communication;
    a pen needle assembly mounted to the distal end of the reservoir housing;
    a needle securely mounted to the pen needle assembly in fluid communication with the secondary reservoir and extending distally from the pen needle assembly; and
    a needle stop having a skin-engaging surface disposed in a preselected position with respect to the pen needle assembly such that a preselected portion of the needle extends distally from the skin-engaging surface;
    wherein the reservoir housing further comprises a lower sleeve slidingly engaged to an upper sleeve, and movable from a first position to a second position; and
    a sliding seal operably engaged to the lower housing and disposed, at least in part, within the secondary reservoir for sliding movement.

21. The apparatus of claim 20, wherein the pen needle assembly is selectively and directly mounted to the reservoir housing.

22. The apparatus of claim 20, wherein the pen needle assembly is fixedly mounted to the reservoir housing.

23. The apparatus of claim 20, wherein the needle stop is integrally formed with either the pen needle assembly or the reservoir housing.

* * * * *

UNITED STATES PATENT AND TRADEMARK OFFICE
CERTIFICATE OF CORRECTION

PATENT NO. : 7,645,264 B2
APPLICATION NO. : 11/102874
DATED : January 12, 2010
INVENTOR(S) : Marsh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1244 days.

Signed and Sealed this

Sixteenth Day of November, 2010

David J. Kappos
*Director of the United States Patent and Trademark Office*